United States Patent [19]

Oesterhelt et al.

[11] Patent Number: 5,290,699
[45] Date of Patent: Mar. 1, 1994

[54] DOUBLE MUTANTS OF BACTERIORHODOPSIN

[75] Inventors: Dieter Oesterhelt; Susanne Meessen; Jorg Tittor, all of Munich; Anja Matuszak, Singen; Klaus May, Munich, all of Fed. Rep. of Germany

[73] Assignee: Max-Planck-Gesellschaft zur Foerderung der Wissenschaften e.V., Goettingen, Fed. Rep. of Germany

[21] Appl. No.: 791,858

[22] Filed: Nov. 14, 1991

[30] Foreign Application Priority Data

Nov. 23, 1990 [DE] Fed. Rep. of Germany ....... 4037342

[51] Int. Cl.$^5$ ...................... C12N 1/21; C12N 15/74; C07K 13/00
[52] U.S. Cl. .............................. 435/252.3; 435/317.1; 435/320.1; 530/350
[58] Field of Search .................. 435/69.1, 71.2, 172.3, 435/252.3, 320.1, 317.1; 530/300, 350; 935/22, 24, 66, 72

[56] References Cited

PUBLICATIONS

Mogi et al., "Aspartic Acid Substitutions affect proton translocation by bacteriorhodopsin," PNAS USA, 85:4148–4152. (Jun. 1988).
Butt et al., "Aspartic Acids 96 and 85 play a central role in the function of bacteriorhodopsin as a proton pump," EMBO J., 8(6):1657–1663. (1989).
Ni et al, "An efficient system for the synthesis of bacteriorhodopsin in Halobacterium halobium," Gene 90:169–172. (1990).
Oesterhelt et al., "Two pumps, one principle: light driven ion transport in Halobacteria," TIBS 14:57–61. (Feb. 1989).
D. Oesterhelt and Stoechenius, Methods Enzymol. 31, Biomembranes (1974), pp. 667–678, "Isolation of the Cell Membrane of Halobacterium halobium and Its Fractionation into Red and Purple Membrane".
Biosystems 19 (1986), pp. 223–236, "The Bacteriorhodopsin Model Membrane System as a Prototype Molecular Computing Element".
Soppa et al., J. Biol. Chem., 264, 22 (1989), pp. 13049–13056, "Bacteriorhodopsin Mutants of Halobacterium sp. GRB".
Subramaniam et al., Proc. Natl. Acad. Sci. USA, 87 (1990), p. 1013–1017, "Protonation state of Asp (Glu-)-85 regulates the purple-to-blue transition in bacteriorhodopsin mutants Arg-82→Ala and Asp-85→Glu: The blue form is inactive in proton translocation".
Dassarma et al., Proc. Natl. Acad. Sci. USA, 81 (1984), p. 125–129, "Bacterio-opsin mRNA in wild-type and bacterio-opsin-deficient Halobacterium halobium strains".
Cline et al., J. Bacteriol. 171 (1989), pp. 4987–4991, "Transformation of the Archaebacterium Halobacterium volcanii with Genomic DNA".
Cline et al., Can. J. Microbiol 35 (198), pp. 148–152, "Transformation methods for halophilic archaebacteria".
Hackett and Dassarma, Can. J. Microbiol 35 (1989), pp. 86–91, "Characterization of the small endogenous plasmid of Halobacterium strain SB3 and its use in transformation of H. halobium".
Lam and Doolittle, Proc. Natl. Acad. Sci. USA, 86 (1989), pp. 5478–5482, "Shuttle vectors for the archaebacterium Halobacterium volcanii".
Stanssens et al., Nucleic Acid. Res. 17 (1989), pp. 4441–4454, "Efficient oligonucleotide-directed construction of mutations in expression vectors by the gapped duplex DNA method using alternating selectable markers".
Bamberg et al., Biochim. Biophys. Acta 773 (1984), pp. 53–60, "Reconstitution of the light-driven electrogenic ion pump halorhodopsin in black lipid membranes".

Primary Examiner—Richard A. Schwartz
Assistant Examiner—James Ketter
Attorney, Agent, or Firm—Collard & Roe

[57] ABSTRACT

Double mutants of bacteriorhodopsin are mutated in the amino acid positions 85 and 96 and are expressed in Halobacteria. The mutants have an altered absorption maximum of their ground state and of their intermediate with the longest life. These mutants pump anions in place of protons.

8 Claims, 5 Drawing Sheets

5' -  G CAA CGC GAG GTT* TAA CAA CAA CAG

CGG CGT GGT GAA CAG CCA GTT* AGC GTA

CCG CGC CCA GTA GAT GGG - 3'

FIG. 5

DOUBLE MUTANTS OF BACTERIORHODOPSIN

BACKGROUND OF THE INVENTION

The present invention relates to double mutants of bacteriorhodopsin, wherein the amino-acid positions 85 and 96 of the opsin of a wild-type strain of Halobacteria are mutated.

2. The Prior Art

Bacteriorhodopsin is a photoactivatable proton pump which occurs in Halobacteria such as, for example, *Halobacterium halobium,* and is composed of a protein portion (bacterioopsin) and of a chromophore (retinal) (see, for example, Oesterhelt and Tittor, TIBS 14 (1989), pp. 57-61). Native bacteriorhodopsin, which is obtainable from the wild type of Halobacterium, has an absorption maximum at a wavelength of 570 nm.

The absorption maximum of the intermediate in the excited state has a wavelength of 412 nm. Bacteriorhodopsin is organized in two-dimensional crystalline regions of the cell membrane, called the purple membrane. Up to 80 percent of the cell membrane of *Halobacterium halobium* may be composed of this purple membrane. Isolation of the bacteriorhodopsin in the form of this purple membrane is possible by known means (Oesterhelt and Stoeckenius, Methods Enzymol. 31 Biomembranes, pp. 667-678, 1974).

Besides bacteriorhodopsin, Halobacteria produce halorhodopsin, a light-driven chloride, bromide and iodide pump. The structure of the latter closely resembles that of bacteriorhodopsin, but it is not produced in cell membrane structures resembling the purple membrane. The content of halorhodopsin in the cell membrane is only one tenth of that of bacteriorhodopsin. The isolation of this halorhodopsin is significantly more elaborate because of these properties. Like bacteriorhodopsin, halorhodopsin has a photocycle, and the absorption maximum of the ground state is at a wavelength of 578 nm. The intermediate with the longest life has an absorption maximum of 520 nm.

Because of the optoelectrical properties of bacteriorhodopsin and other rhodopsins, attempts are being made to use these substances for biocomputers and for pattern recognition (Biosystems 19 (1986), pp. 223-236). It is desirable, for these purposes, to shift the absorption maximum of bacteriorhodopsin and of the intermediate in the photocycle to longer wavelengths in order to be able to replace the costly special lasers which are required for the excitation of the wild-type bacteriorhodopsin by low-cost commercially available lasers.

The property of halorhodopsin of being able, with the aid of light energy, to pump chloride ions would be interesting for an application for the desalination of solutions. To date, the isolation of halorhodopsin has been so elaborate that no economic utilization has been possible. It is, therefore, desirable to be able to isolate rhodopsins with the properties of halorhodopsin in the form of purple membranes.

To date, several mutants of bacteriorhodopsin which have shown an effect of the mutation on the photocycle and the absorption maxima have been disclosed.

Mogi et al (PNAS USA 85, 4148-152, 1988) describe single amino-acid mutants in which the amino acid Asp in positions 85, 96, 115 and 212 is replaced by Glu or Asn. In other mutants, Asp in position 212 is replaced by Asn, Glu or Ala. The proteins were expressed in *E. coli.* The proteins were purified from *E. coli.* Bacteriorhodopsin-like chromophores were regenerated by detergent, phospholipid treatment and addition of retinal. It was shown that proton translocation was completely abolished by replacement of Asp-85 with Asn and partly (<10%) by replacement of Asp-96 by Asn and Asp-212 by Glu. Mutation of Asp-85 to Asn resulted in a shift in the absorption maximum to $\lambda_{max}=590$ nm.

Soppa et al [*J. Biol. Chem.,* 264, 22, 13049-13056, (1989)] describes bacteriorhodopsin muteins with the following single amino-acid mutations Asp-85 to Glu; Asp-96 to Asn; Asp-96 to Gly. These muteins were generated by random mutagenesis with X-ray or UV radiation and selected by bromodeoxyuracil selection of photosynthetically negative phenotypes. Thus, they were not generated in a directed manner. These muteins differed from the modified proteins investigated by Mogi et al in that they were expressed in Halobacteria and isolated therefrom in structures resembling purple membranes. Mutation of Asp-96 slowed down the kinetics of the photocycle. No alteration in the spectral properties of bacteriorhodopsin occurred in this case. Replacement of amino acid Asp-85 by Glu results in a shift in the absorption maximum from 568 nm to 610 nm. Deprotonation of amino acid Glu-85 shifts the absorption maximum to about 530 nm.

Subramaniam et al [Proc. Natl. Acad. Sci USA, 87, pp. 1013-1017, (1990)] investigated the change in the absorption spectrum of bacteriorhodopsin by mutations at position Asp-85 and Arg-82. Replacement of Asp-85 with Asn yields a blue chromophore ($\lambda_{max}=588$ nm). Proton translocation is no longer detectable. No investigations of the photocycle were carried out.

SUMMARY OF THE INVENTION

It is an object of the present invention to prepare bacteriorhodopsin mutants which have both an absorption maximum which is shifted to longer wavelength ranges and a photocycle in which the intermediate with the longest life has an absorption maximum: >500 nm.

It is another object of the present invention to prepare a bacteriorhodopsin mutein which pumps anions.

It is yet another object of the present invention to express this bacteriorhodopsin mutein efficiently, in biologically active form, and to be able to isolate it in the form of a two-dimensional lipid protein crystal "purple membrane."

In a preferred embodiment of the invention, the amino-acid positions 85 and 96 of this opsin are mutated from Asp to Asn (D85,96N).

In another preferred embodiment of the invention, the opsin originates from the wild-type strain of *Halobacterium halobium.*

The present invention further relates to multiple mutants of bacteriorhodopsin, which carry out light-driven pumping of anions.

The present invention furthermore comprises multiple mutants of bacteriorhodopsin, whose absorption maximum is greater than 578 nm.

The present invention also relates to the "purple membranes" from the strains of Halobacteria which produce the bacteriorhodopsin mutants according to the invention.

The present invention furthermore comprises a process for preparing a strain of Halobacteria which produces a multiple mutant of bacteriorhodopsin, which comprises: (1) subjecting an opsin gene to directed mutagenesis; (2) transforming cells of a strain of Halobacterium wherein the opsin gene corresponding to the opsin gene mutated in step (1) is inactive, or which lacks the bop gene and other retinal protein genes, with a recombinant halobacterial vector which contains at least one copy of the opsin gene mutated in step 1; and (3) regenerating and cultivating the transformed *Halobacterium halobium* cells.

The items to which the invention relates can be employed for optical information processing using holographic methods. Examples are real-time interferometry, pattern recognition and reversible holographic information storage. Another possible use is employment for desalinating salt-containing solutions.

According to the present invention, a defined opsin gene undergoes directed mutagenesis. The directed mutagenesis takes place outside the *H. halobium* cells using methods known per se to a person skilled in the art of molecular biology (for example, oligonucleotide-directed mutagenesis, chemical DNA synthesis or PCR reaction). The term "mutagenesis" refers to the replacement of two or more nucleotides in an opsin gene, which, in turn, results in a specific replacement of amino-acid residues in the resulting gene product, the retinal protein. The mutagenesis of bacteriorhodopsin preferably affects the amino acids which form the ion-conducting channel or, preferably, the amino acids which are involved in retinal binding and thus influence color and photocycle. Mutations are particularly preferably introduced in positions 85 and 96 of opsin.

It is essential to the invention for the expression of the muteins in Halobacterium that a *Halobacterium halobium* strain wherein the opsin gene corresponding to the particular mutated opsin gene is inactive, or which lacks the bop gene and other retinal protein genes, is used for the transformation The opsin gene can have been inactivated, for example, by genetic insertion, deletion or other alteration, so that the bacterial strain is no longer able to express a functional opsin in the cell. However, the cells must be able to synthesize retinal, which can link in the transformed cell as pigment with the opsin, to give the particular retinal protein. An example of a suitable bacterial strain is *H. halobium* IV-8, which contains an ISH1 insertion in the bacterioopsin gene [Betlach et al., Appl. Microbiol. 7 (1986), pp. 83-89]. Likewise very suitable is the *H. halobium* strain L33 (DSM 5735) which contains an ISH2 insertion within the bacterioopsin gene [DasSarma et al, Proc. Nat. Acad. Sci. USA 81 (1984), pp. 125-129] or HN5 (BR− HR− insert) (DSM 6229). The *H. halobium* strain L33 is distinguished in that this strain has for years proven to be stable, despite the known extremely high spontaneous mutation rates of *H. halobium*, in general. In HN5 also, as in the strain L33, the bacterioopsin gene (bop) is inactivated by an insertion element about 1 kb in size. The insertion element is located in the amino-terminal part or in the promoter region of the bop gene. However, in addition, there is in HN5 an insertion element about 1 kb in size in the region of the hop gene, which codes for the protein portion of the halorhodopsin. These insertions make the strain HN5 phenotypically bacteriorhodopsin- and halorhodopsin-negative.

The following three microorganisms were each deposited under the provisions of the Budapest Treaty at the DSM Deutsche Sammlung Von Mikroorganism Und Zellkulturen GmbH, having the address of Mascheroder Weg 1 B, D-3300 Braunschweig, Germany, as follows.

| Microorganism | Accession Number | Date of Deposit |
| --- | --- | --- |
| (a) plasmid p319/D85,96N | DSM 6225 | October 31, 1990 |
| (b) Halobacterium HN5 | DSM 6229 | October 31, 1990 |
| (c) *Halobacterium halobium* L33 | DSM 5735 | January 3, 1990 |

The above-described deposited microorganisms will irrevocably, and without restriction or condition, be released to the public as of the issue date of a U.S. patent granted for the above-identified patent application.

To transform Halobacteria, first it is necessary to prepare spheroblasts. This can be carried out in a conventional way, as described, for example, by Cline et al [J. Bacteriol. 171 (1989), pp. 4987-4991] or by Ni et al [Gene 90 (1990), 169-172].

*H. halobium* can be transformed with bacteriophage DNA, plasmid DNA and linear genomic DNA, see, Cline et al, [Can. J. Microbiol. 35 (1989), 148-152]. It is, thus, in principle, possible to use bacteriophages, plasmids or linear DNA molecules as recombinant halobacterial vectors for the process according to the invention. Plasmids are preferably used to insert a mutated opsin gene into *H. halobium* spheroblasts. Examples of plasmid vectors suitable, in principle, for transformation of *H. halobium* are described by Hackett and DasSarma [Can. J. Microbiol. 35 (1989), 86-91]. It is possible to clone an opsin gene, which may already be mutated, into a plasmid of this type in a conventional manner. If a bacteriorhodopsin mutein is to be expressed, the vector can, where appropriate, contain the brp gene from *Halobacterium halobium*, in addition to the bacterioopsin gene (bop). Furthermore, it is possible to introduce modifications in the vicinity of the structural gene (for example, promoter region) to increase the expression of the gene product. A halobacterial vector used for the process according to the invention preferably contains a selection marker, so that better selection for transformed cells is possible A selection marker which can be used for Halobacteria is located, for example, on the plasmid pH455 [Lam and Doolittle, Proc. Nat. Acad. Sci. USA 86 (1989), pp. 5478-5482]. A 15.8 kb HindIII fragment of plasmid pH455 contains a gene which brings about resistance to the HMG-CoA reductase inhibitor mevinolin (Monakolin K) (3α-methylcompactin) in *H. halobium* and *H. volcanii*. Particularly preferred is a so-called Halobacterium-*E. coli* shuttle vector which additionally contains genetic elements which permit replication and selection in *E. coli*.

The presence of a halobacterial selection marker on the vector is preferred, but is not absolutely necessary, because the selection for positively transformed cells can also occur by the change in color of the cells caused by the expression of the retinal protein.

In a particularly preferred embodiment of the process according to the invention, mutated derivatives of the recombinant plasmid p319 are used as halobacterial vector. The details of the construction of a mutated derivative of p319 are described in the examples and in the figures.

The transformation of *H. halobium* with plasmid DNA is known, in principle, see, Cline et al [Can. J. Microbiol. 35 (1989), pp. 148-152]; Ni et al [Gene 90 (1990), pp. 169-172].

SEQ ID NO: 1 reproduces the nucleotide sequence of the mutated oligonucleotide D85,96N. The sequence complementary to the RNA is depicted.

The following abbreviations are used in the figures:
cat*: inactive chloramphenicol acetyltransferase gene
bla*: inactive ampicillin-resistance gene (bla gene)
Ap$^s$: ampicillin-sensitive
cat: active chloramphenicol acetyltransferase gene
bla: active ampicillin-resistance gene (bla gene)
CmR: chloramphenicol-resistant
bop**: mutated bop gene D85,96N

BRIEF DESCRIPTION OF THE DRAWINGS

Other objects and features of the present invention will become apparent from the following detailed description considered in connection with the accompanying drawings and examples, which disclose one embodiment of the present invention. It should be understood, however, that the drawings and examples are designed for the purpose of illustration only, and not as a definition of the limits of the invention.

* indicates the positions in which C has been replaced by T.

DETAILED DESCRIPTION OF THE PREFERRED EMBODIMENT

Examples

In vitro mutagenesis of the bop gene, transformation of a bop-negative strain of *H. halobium* with a vector which harbors the mutated bop gene, and detection of the expression of modified bacteriorhodopsin are shown in the examples.

1. Mutagenesis

Figure 1:
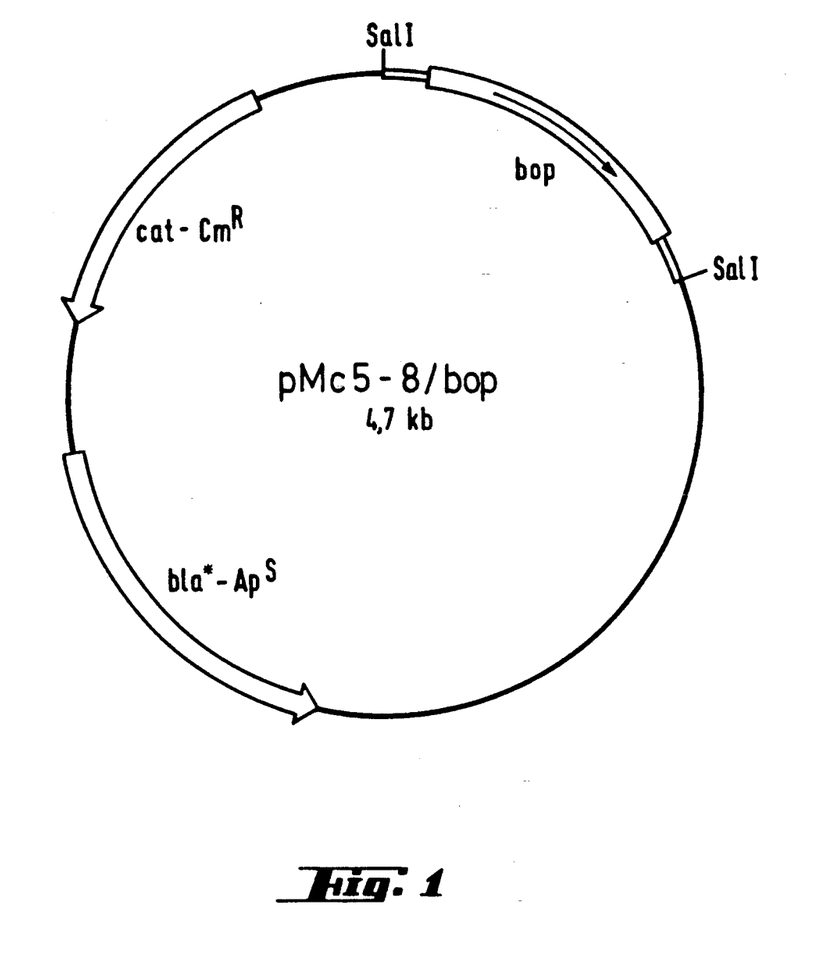
FIG. 1 shows the restriction map of the plasmid Mc5-8/bop.
Figure 2:
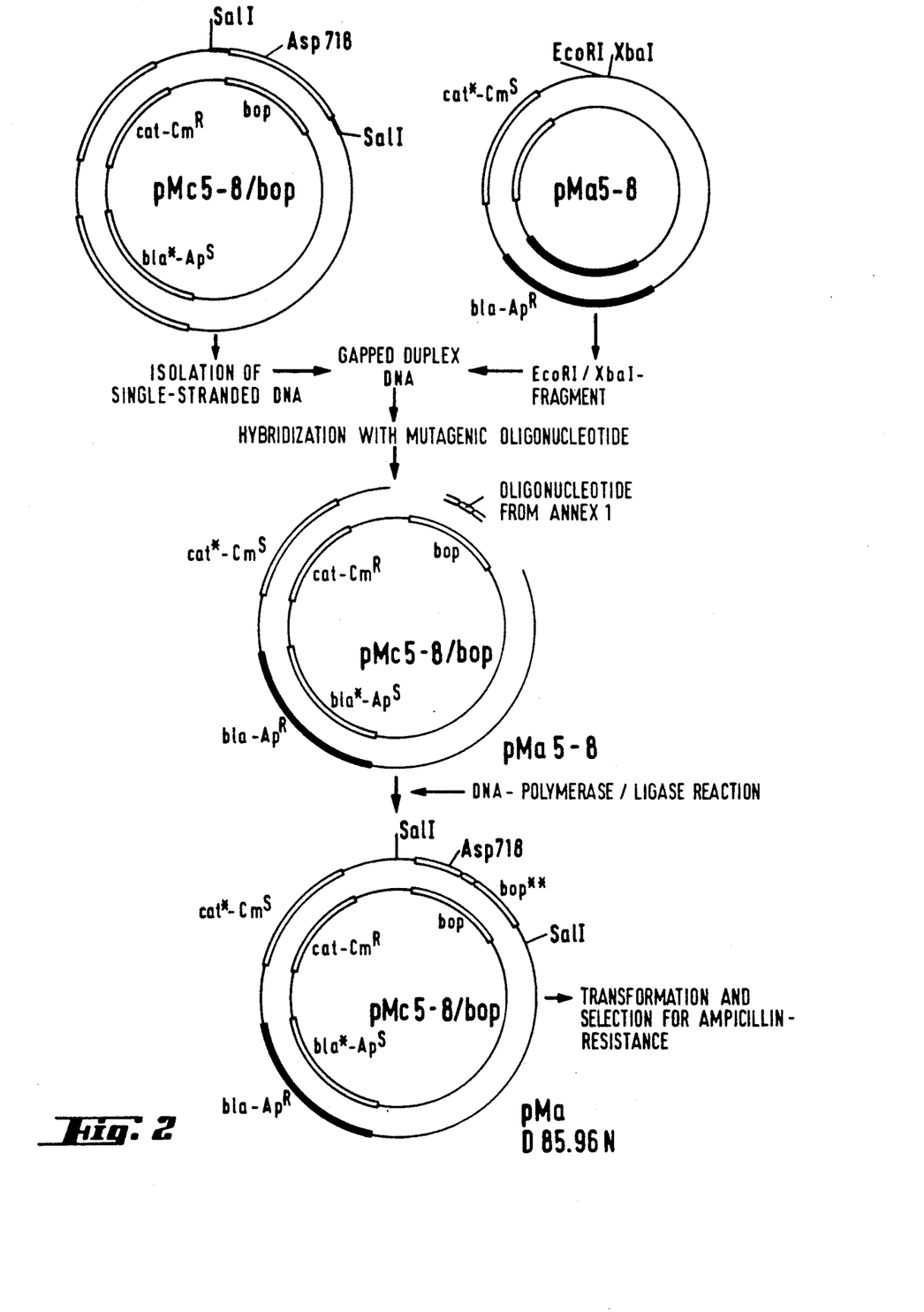
FIG. 2 is a diagrammatic representation of the mutagenesis of the native bop gene.
Figure 5:
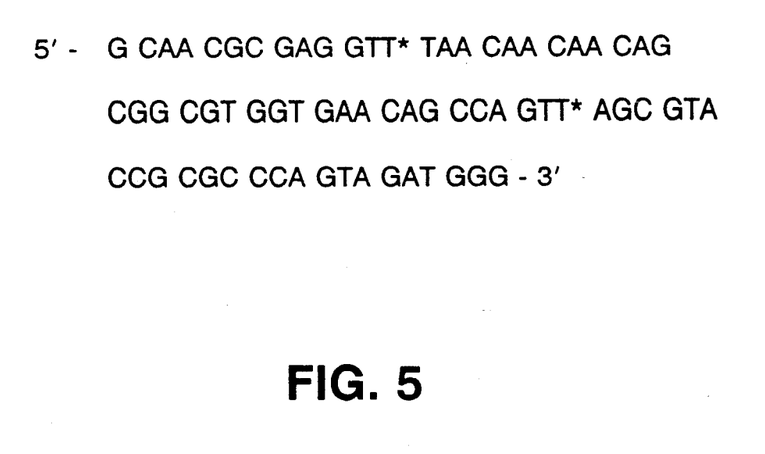
FIG. 5 shows the nucleotide sequence of the mutated oligonucleotide D85,96N of SEQ ID NO: 1.

The plasmid pMc5-8/bop (FIG. 1) is composed of a SalI fragment which is 0.9 kb in size, with the bop gene from *H. halibium* which has been cloned in the SalI-cut mutagenesis vector pMc5-8 [Stanssens et al, Nucleic Acids Research 17, pp. 4441–4454, (1989)]. The resulting plasmid pMc5-8/bop (FIG. 1) has an inactive ampicillin-resistance gene (bla*) and an active chloramphenicol acetyltransferase gene (cat). pMc 5-8/bop was mutated by the method described by Stanssens et al [Nucleic Acids Research 17, pp. 4441–4454 (1989)](FIG. 2). For this, single-stranded DNA was isolated from pMc5-8/bop and hybridized with the EcoRI/XbaI fragment of pMa5-8. The plasmid pMa 5-8 harbors an inactive chloramphenicol acetyl-transferase gene (cat*) and an active ampicillin-resistance gene (bla). To prepare the gapped duplex DNA, a mixture composed of the pMa5-8 fragment (0.1 pmol) and of the single-stranded DNA (0.5 pmol) was incubated in a volume of 36 μl at 70° C. for 5 min and then cooled to room temperature by addition of 4 μl of hybridization buffer (1.5 M KCl, 100 mM Tris/Cl pH 7.5) - heated to 70° C. 8 μl of this mixture were then mixed with 4 to 10 pmol of mutagenic oligonucleotide (2 μl), heated at 65° C. for 5 min for the hybridization, and cooled to room temperature. The 70-mer oligonucleotide employed for the mutagenesis codes for Asn at position 85 and 96 bop gene, each case, instead for Asp (FIG. 5/SEQ ID No: 1). For the DNA polymerase/ligase reaction, 4 μl of 10×buffer (625 mM KCl, 275 mM Tris-HCl, 150 mM MgCl$_2$, 20 mM DTT, 0.5 mM ATP, 0.25 mM of each of the four dNTPs, pH 7.5) were added to the mixture, which was made up to 40 μl with H$_2$O and, after addition of 1 unit of DNA polymerase (Klenow fragment) and 5 units of T4 DNA ligase, incubated at room temperature for 45 min. After transformation of the DNA polymerase/ligase mixture, the different resistance markers on the two strands were used to select for the mutant strand (ampicillin resistance). This resulted in the plasmid pMaD85,96N (FIG. 2, 3). This plasmid contains the bop gene mutated in position 85 and 96.

2. Recloning of the Mutated Bop Gene for Expression in *Halobacterium Halobium*

(a) *E. coli* vector

Figure 3:
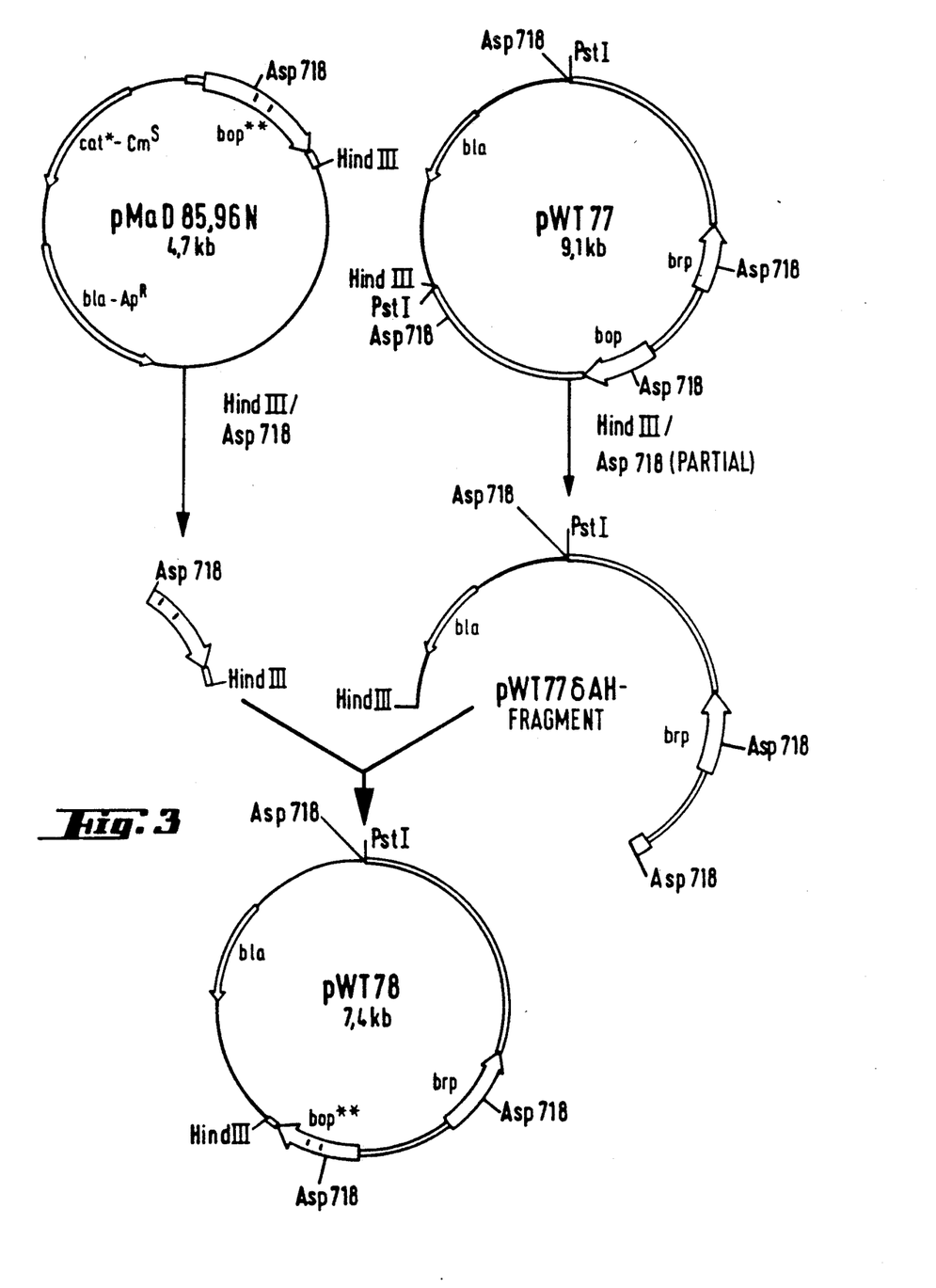
FIG. 3 shows the construction of pWT78.

FIG. 3 describes the construction of pWT78 from the plasmids pMaD85,96N and pWT77. The plasmid pWT77 is the commercially available *E. coli* plasmid pGEM4 into whose PstI restriction site has been cloned a halobacterial PstI fragment with the wild-type bop gene and brp gene. pWT77 was linearized with HindIII and partially cleaved with Asp718. The 6.8 kb HindIII/Asp718 fragment WT77δAH, with the vector position (pGEM4) and the 5' region of the wild-type bop gene was ligated to the HindIII/Asp718 fragment from pMaD85,96N which contains the mutated 3' region of the bop gene. This results in the plasmid pWT78 which is 7.4 kb in size.

(b) *E. coli*-Halobacterium Vector

Figure 4:
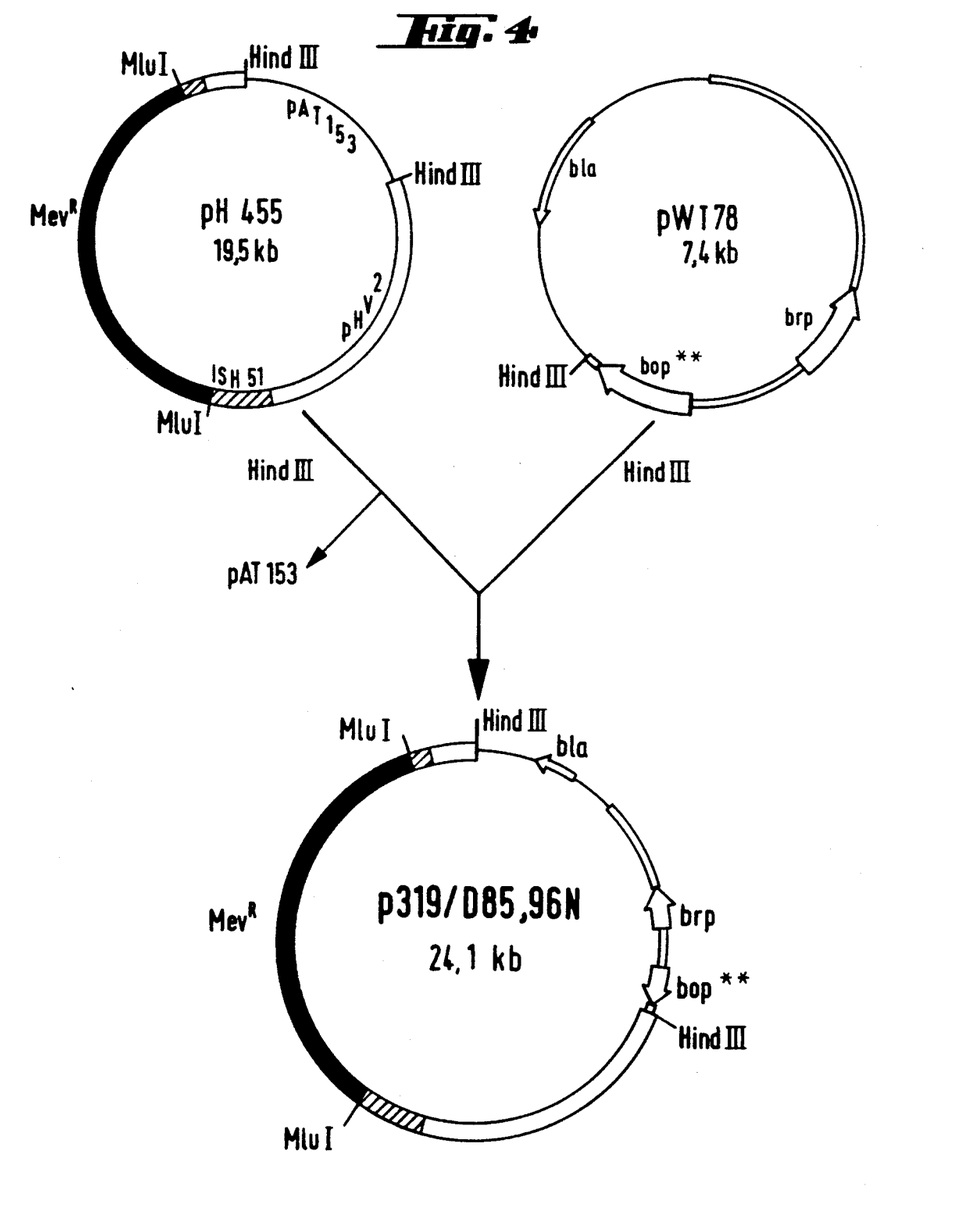
FIG. 4 shows the construction of p319/D85,96N.

The plasmid p319/D85,96N was used for expression of the mutated bop gene in *Halobacterium halobium*. The construction is shown in FIG. 4 and is analogous to the construction of the plasmid p319 described by Ni et al. [Ni et al, Gene 90 (1990) 169–172]. The plasmid pH455 has been described by Lam and Doolittle [Proc. Nat'l. Acad. Sci. USA 86, (1989) 5478∝5482]. This plasmid contains the mevinolin-resistance gene ISH51-DNA and the endogenous *Halobacterium volcanii* plasmid pHV2, in addition to *E. coli* portions (pAT153). pH455 was cleaved with HindIII, and the fragment of about 16 kb which contains the mevinolin-resistance gene and the pHV2 portion was ligated to the HindIII-linearized plasmid pWT78. The resulting plasmid p319/D85,96N (DSM 6225) was used for the transformation of *Halobacterium halobium* L33.

3. Transformation and Expression

The strain *Halobacterium halobium* L33 (DSM 5735) was used for the transformation. The transformation was carried out by the method developed by Ni et al., Gene 90 (1990) 169–172.

(a) Spheroplast formation 1 ml of a 35 ml cell culture (about 90 Klett units) of *Halobacterium halobium* L33 (DSM 5735) in growth medium (250 g of NaCl, 20 g of MgSO$_4$. 7H$_2$O, 3 g of trisodium citrate . 2H$_2$O, 2 g of KCl, 0.2 g of CaCl$_2$. 2H$_2$O, 25 ml of 2 mol/l tris-HCl pH 7.2, 3 g of yeast extract (Difco), 5 g of tryptone (Difco) and H$_2$O ad 1000 ml) is centrifuged in 1.5 ml Eppendorf tubes at 3000 to 4000 rpm, at room temperature, for 15 minutes. The supernatant is removed as completely as possible with a Pasteur pipette. The cells are taken up in 100 μl of spheroblast-forming solution (SPH: 2 mol/l NaCl, 25 mmol/l KCl, 50 mmol/l tris-HCl pH 8.75, 15 percent sucrose, sterile filtered). Subsequently, 10 μl of 0.5 mol/l EDTA in SPH are pipetted onto the upper inside rim of the vessel and combined with the cell suspension by rapid mixing (rotation of the Eppendorf tube).

The spheroblasts are formed within about 30 minutes at room temperature, and it is possible to check the completeness of spheroplast formation under a light microscope.

(b) Transformation of the Spheroblasts

The DNA is added in a volume of 20 μl (composed of 15 μl of DNA solution (10 μg in 15 μl of 50 mM tris Cl, pH 7.5, 1 mM EDTA) and 5 μl of 0.5 mol/l EDTA in SPH) to the spheroplast suspension and incubated at room temperature for 5 minutes. Between 3 and 10 μg of plasmid DNA were employed per transformation mixture. The polyethylene glycol solution (240 μl) was placed in the lid of the Eppendorf tube and combined with the SPH suspension by rapid mixing. Incubation is carried out at room temperature for 20 minutes.

The polyethylene glycol solution is composed of: 60 percent (v/v) PEG 600 (Sigma) and 40 percent SPH. The PEG 600 used was purified, in some cases, as follows.

The purification of PEG 600 is based on the procedure of Klebe et al, Gene 25 (1983) 333 et seq. 30 g of PEG 600 were dissolved in 30 ml of benzene. 60 ml of isooctane were added to the PEG 600/benzene mixture which is then placed on ice for 30 min. The PEG 600 solidified, and it was then possible to decant off the upper organic phase. The PEG 600 was warmed to room temperature in a water bath. Once again, 60 ml of isooctane were added to the PEG 600, and the mixture was vigorously shaken and left to stand at room temperature overnight. The isooctane phase was discarded, and the PEG 600 was extracted by shaking twice with 150 ml of diethyl ether in a separating funnel. The diethyl ether was then removed in a rotary evaporator (about 2 h).

(c) Regeneration of the Transformed Spheroblasts

The transformation mixture is diluted with 1 ml of regeneration solution (REG: 3.5 mol/l NaCl, 150 mmol/l MgSO$_4$ . 7H$_2$O, 50 mmol/l KCl, 7 mmol/l CaCl$_2$ . 2H$_2$O, 50 mmol/l tris HCl, pH 7.2, 15 percent sucrose, filter sterile), mixed and centrifuged as indicated above. The supernatant is then completely removed with a drawn-out Pasteur pipette, and the bacterial pellet (often not visible) is cautiously suspended in 1 ml of complete medium (mixture of 80 ml of H$_2$O with 250 g/l NaCl, 20 g/l MgSO$_4$ . 7H$_2$O, 3 g/l trisodium citrate . 2H$_2$O, 2 g/l KCl, 0.2 g/l CaCl$_2$ . 2H$_2$O and 30 ml of H$_2$O with 18 g of sucrose, 0.6 g of tryptone, 0.4 g of yeast extract, filter sterile) and incubated at 37° C. overnight.

(d) Plating Out 0.1 to 0.25 ml portions of the cells are taken up in 3 ml of freshly prepared overlay medium (25 g NaCl, 2 g MgSO$_4$ 7H$_2$O, 0.3 g trisodium citrate . 2H$_2$O, 0.2 g KCl, 0.02 g CaCl$_2$ . 2H$_2$O made up to 85 ml with H$_2$O and adjusted to pH 7.2; 0.3 g yeast extract, 0.5 g tryptone, 0.8 g agar made up to 15 ml; both components autoclaved, mixed and 15 g sucrose/100 ml solution and mevinolin added to a final concentration of 20 μmol/l at 56° C.) at about 45° C. This suspension is immediately poured into support plates (250 g NaCl, 20 g MgSO$_4$ . 7H$_2$O, 3 g trisodium citrate . 2H$_2$O, 2 g KCl made up to 850 ml; 3 g yeast extract, 5 g tryptone, 1.5 percent agar made up to 350 ml, both autoclaved, mixed after autoclaving and mevinolin added to a final concentration of 20 μmol/l).

The plates are sealed and left in an incubator at 40° C. for at least 4 weeks.

4. Culture of the Transformants and Isolation of the Mutated Bacteriorhodopsin Colonies of transformed cells, which often do not appear for weeks, are greenish in color, in contrast to the colonies of spontaneously mevinolin-resistant cells (yellowish), and are grown in 35 ml of complete medium which contains 20 μmol/l mevinolin. It is possible by cloning to isolate from the cell mixture homologous recombinants which make it unnecessary to add mevinolin to the medium.

The BR mutein with the amino-acid replacements of Asp with Asn at pos. 85 and 96 (D85,96N) is isolated by sucrose density gradient centrifugation, as described in Oesterhelt and Stoeckenius [Methods Enzymol. 31, Biomembranes, 667-678, (1974)]. The protein is obtained as a blue membrane with a flotation density like the purple membrane of the wild type.

5. Characterization of the Bacteriorhodopsin Muteins

The membrane fraction which contains as sole protein the BR mutein D85,96N has a flotation density of about 1.2 g/cm$^3$, which corresponds to that of the purple membrane The absorption maximum of the protein is at 608 nm (10 mM tris buffer pH 7.0). The pK value of the Schiff's base of the retinal is reduced from the 13 of the wild type to 8.5 in salt concentrations exceeding 1 M NaCl and corresponds, just like the absence of an M intermediate in the photocycle, to the behavior of halorhodopsin. In place of the M intermediate with a deprotonated Schiff's base, the intermediate with the maximum blue shift which occurs is a species which has a difference maximum at 535 nm in photometric determinations. The initial state is repopulated in 5 ms.

The BR mutein D85,96N-containing membrane was adsorbed onto black film membranes and examined by the method described by Bamberg et al (Biochim, Biophys. Acta 773, 53–60, 1984). The chloride-dependent, photo-induced stationary currents measured in this way demonstrate that the mutein has not only the photochemical properties of halorhodopsin, but also its ion-translocational activity.

While only a single embodiment of the present invention has been shown and described, it is to be understood that many changes and modifications may be made thereunto, without departing from the spirit and scope of the invention as defined by the appended claims.

---

What is claimed is:

1. A bacteriorhodopsin protein comprising:
bacteriorhodopsin having aspartic acid mutated to asparagine in amino acid positions 85 and 96 of the opsin of a wild-type strain of Halobacteria.

2. The protein as claimed in claim 1 wherein the gene encoding said opsin originates from the wild-type strain of *Halobacterium, halobium*.

3. A strain of Halobacteria which produces the bacteriorhodopsin according to claim 1.

4. A cell membrane fragment containing said protein from the strain of Halobacteria according to claim 3.

5. The *H. halobium* strain HN5 (DSM 6229).

6. A strain of Halobacteria which produces the bacteriorhodopsin according to claim 1.

7. A cell membrane fragment containing said protein from a strain of Halobacteria according to claim 6.

8. The vector p319/D85,96N (DSM 6225).

* * * * *

SEQUENCE LISTING ( 1 ) GENERAL INFORMATION:

-continued (iii) NUMBER OF SEQUENCES:1

(2) INFORMATION FOR SEQ ID NO: 1:

(i) SEQUENCE CHARACTERISTICS:
        (A) LENGTH:70 base pairs
        (B) TYPE:nucleic acid
        (C) STRANDEDNESS:single
        (D) TOPOLOGY:linear     (ii) MOLECULE TYPE:DNA (genomic)

(xi) SEQUENCE DESCRIPTION: SEQ ID NO: 1:

```
      G CAA CGC GAG GTT TAA CAA CAA CAG            25
      CGG CGT GGT GAA CAG CCA GTT AGC GTA          52
      CCG CGC CCA GTA GAT GGG                      70
```